United States Patent [19]

Suh

[11] 3,952,036

[45] Apr. 20, 1976

[54] 1,1-(THIADIALKYLIDENE) FERROCENE S-OXIDES

[75] Inventor: John T. Suh, Mequon, Wis.

[73] Assignee: Richardson-Merrell Inc., Wilton, Conn.

[22] Filed: Sept. 9, 1974

[21] Appl. No.: 504,366

[52] U.S. Cl. .......................... 260/439 CY; 424/295
[51] Int. Cl.² .......................................... C07F 15/02
[58] Field of Search ................. 260/439 CY, 607 A

[56] References Cited
UNITED STATES PATENTS

| | | | |
|---|---|---|---|
| 3,382,267 | 5/1968 | Suh | 260/439 CY |
| 3,792,095 | 2/1974 | Burmistrouh | 260/607 A |
| 3,804,904 | 4/1974 | Bentley et al. | 260/607 A |

OTHER PUBLICATIONS

Finar, Organic Chemistry, 4th ed., 1963, Longmans, London, p. 338, Vol. 1.

Primary Examiner—Arthur P. Demers
Attorney, Agent, or Firm—L. Ruth Hattan; Eugene O. Retter; George W. Rauchfuss, Jr.

[57] ABSTRACT

The compounds are ferrocene derivatives useful as organo-iron sources and hematinic agents. Compounds disclosed are 1,1'-diethyl-α,α'-thiabiscyclopentadienyl-iron-S-oxide and 1,1'-diethyl-α,α'-thiabiscyclopentadienyl-iron-S-dioxide.

7 Claims, No Drawings

1,1-(THIADIALKYLIDENE) FERROCENE S-OXIDES

My earlier U.S. Pat. No. 3,382,267, which issued May 7, 1968, discloses ferrocene cyclic thioethers which may be employed as starting materials in the preparation of the compounds of the present invention.

DETAILED DESCRIPTION

The novel compounds of the present invention may be represented by the following formulae:

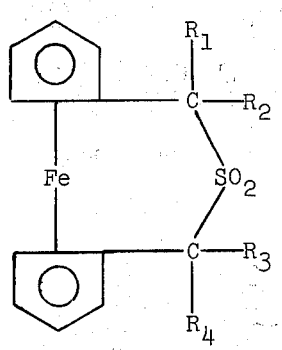

I

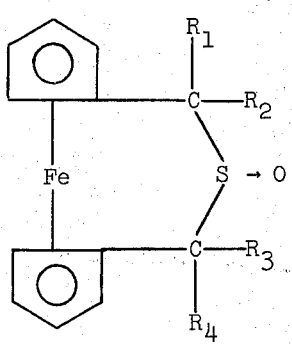

II wherein $R_1$, $R_2$, $R_3$ and $R_4$ are selected from the group consisting of hydrogen, lower alkyl such as methyl, ethyl, isopropyl, butyl and hexyl, an aryl such as phenyl, or a nuclear-substituted phenyl such as halogen-substituted phenyl, an aralkyl such as benzyl, phenethyl, phenylisopropyl, diphenylmethyl, a cycloalkyl, particularly a cycloalkyl having from 3 to 7 carbon atoms such as cyclopropyl, cyclopentyl, cyclohexyl and a cycloalkyl-lower alkyl such as cyclohexylmethyl and cyclopentylethyl.

The novel compounds of Formula I, the S-dioxides, are conveniently prepared by treating a corresponding ferrocene cyclic thioether with a suitable oxidizing agent in acetone. The preferred oxidizing agent is 30 percent hydrogen peroxide solution, but other oxidizing agents such as m-chloroperbenzoic acid, peracetic acid or permanganate may be used. The reaction is preferably conducted under reflux conditions and is essentially complete after about 7 to 9 hours.

The compounds of Formula II, the S-mono-oxides, are conveniently prepared by the same reaction except that the reaction is interrupted after about only two to three hours at reflux or at any other point at which is can be established that the formation of the S-monooxides is essentially complete and that significant formation of the S-dioxides has not occurred. The described processes may be illustrated as follows:

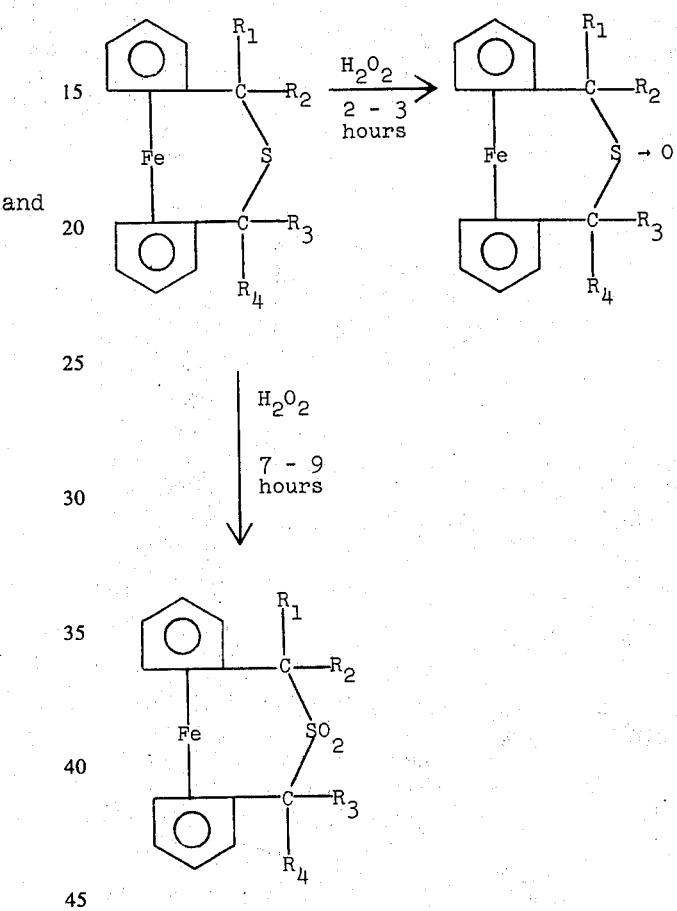

in which $R_1$, $R_2$, $R_3$ and $R_4$ are as previously defined.

Representative of the compounds which may be prepared by the described processes are the following:

1,1'-dimethyl-α,α'-thiabiscyclopentadienyl-iron-S-oxide, 1,1'-dimethyl-α,α'-thiabiscyclopentadienyl-iron-S-dioxide, 1,1'-diethyl-α,α'-thiabiscyclopentadienyl-iron-S-oxide, 1,1'-diethyl-α,α'-thiabiscyclopentadienyl-iron-S-dioxide, 1,1'-dipropyl-α,α'-thiabiscyclopentadienyl-iron-S-oxide, 1,1'-dipropyl-α,α'-thiabiscyclopentadienyl-iron-S-dioxide, 1,1'-diisopropyl-α,α'-thiabiscyclopentadienyl-iron-S-oxide, 1,1'-diisopropyl-α,α'-thiabiscyclopentadienyl-iron-S-dioxide, 1,1'-diphenyl-α,α'-thiabiscyclopentadienyl-iron-S-oxide, 1,1'-diphenyl-α,α'-thiabiscyclopentadienyl-iron-S-dioxide,
1,1'-dichlorophenyl-α,α'-thiabiscyclopentadienyl-iron-S-oxide,
1,1'-dichlorophenyl-α,α'-thiabiscyclopentadienyl-iron-S-dioxide,
1,1'-dibenzyl-α,α'-thiabiscyclopentadienyl-iron-S-oxide, and
1,1'-dibenzyl-α,α'-thiabiscyclopentadienyl-iron-S-dioxide.

As previously mentioned, the ferrocene cyclic thioethers which are employed as starting materials are disclosed in U.S. Pat. No. 3,382,267.

The ferrocene S-oxides, in addition to being useful organo-iron sources in chemical reactions, and as polymerizing agents, are effective hematinic agents useful in the treatment of iron deficiencies in animals such as piglets, and humans.

When employed as pharmaceutical agents, the novel compounds are combined with conventional pharmaceutical diluents and formed into dosage forms suitable for oral or parenteral administration such as tablets, capsules, syrups, elixirs and solutions.

Pharmaceutical carriers which are either solid or liquid may be employed. The preferred liquid carrier is water. However, suitable organic solvents such as propylene glycol may be used. Solid pharmaceutical carriers such as starch or sugar may be employed to form powders which can, in turn, be tableted or used to fill capsules. Other pharmaceutical excipients such as lubricants, disintegrating agents and flavoring agents may also be employed.

The unit dosage forms such as tablets or capsules may contain any suitable predetermined amount of the active ingredients and may be administered one or more at a time at specified intervals. Generally, such dosage forms will contain approximately 5 to 100 mg. of the active ingredient.

The exact quantity of the composition to be administered will, of course, depend upon many factors, including the elemental iron content of the compound and the nature and extent of the iron deficiency of the patient.

The following examples illustrate the practice of the present invention:

Example 1

1,1'-Diethyl-α,α'-thiabiscyclopentadienyl-iron-S-oxide

A mixture of 10.0 g. (0.037 mole) of 1,1'-diethyl-α,α'-thiabiscyclopentadienyl-iron and 14.93 g. (0.132 mole) of 30% $H_2O_2$ in 147 ml. of acetone is refluxed for 2.5 hours, after which it is cooled, and filtered through Dicalite. The filtrate is diluted with brine and extracted four times with ether. The combined extracts are washed with brine, dried and concentrated to yield a semi-solid which is recrystallized three times from benzene to yield 1,1'-diethyl-α,α'-thiabiscyclopentadienyl-iron-S-oxide as yellow needles, m.p. 200°–202°.

Anal. Calcd. for $C_{14}H_{16}FeSO$: C, 58.35; H, 5.60.
Found: C, 58.75; H, 5.69.

Example 2

1,1'-Diethyl-α,α'-thiabiscyclopentadienyl-iron-S-dioxide

A mixture of 1.0 g. (0.0035 mole) of 1,1'-diethyl-α,α'-thiabiscyclopentadienyl-iron-S-oxide and 1.98 g. (0.0131 mole) of 30% $H_2O_2$ in 15 ml. of acetone is heated at 40°–55° for 2.5 hours, after which it is left at 22° for 16 hours. The mixture is then heated to reflux and maintained for 2.5 hours, after which an additional 1.48 g. (0.0131 mole) of $H_2O_2$ is added and the refluxing continued for 6.5 hours. The mixture is cooled, filtered, and the filtrate diluted to 125 ml. with water and cooled for 3 days. The precipitated solid is collected and recrystallized from a small amount of 2-propanol to yield 1,1'-diethyl-α,α'-thiabiscyclopentadienyl-iron-S-dioxide as a yellow powder, m.p. 188°–190°.

Anal. Calcd. for $C_{14}H_{16}FeSO_2$: C, 55.27; H, 5.30.
Found: C, 55.40; H, 5.22.

I claim:

1. A compound selected from the compounds of the following formulae:

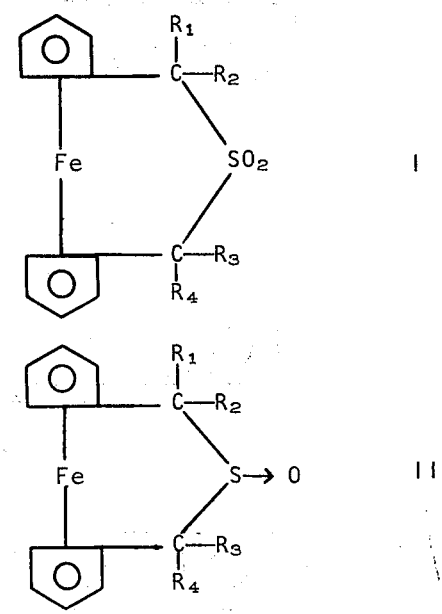

in which $R_1$, $R_2$, $R_3$ and $R_4$ are selected from hydrogen, methyl, ethyl, propyl, isopropyl, butyl, hexyl, phenyl, chlorophenyl, benzyl, phenethyl, phenylisopropyl, diphenylmethyl, and cycloalkyl having from 3 to 7 carbon atoms.

2. A compound of Formula I of claim 1 in which $R_1$ and $R_4$ are alkyl.

3. A compound of Formula II of claim 1 in which $R_1$ and $R_4$ are alkyl.

4. A compound of Formula I of claim 1 in which $R_2$ and $R_3$ are hydrogen.

5. A compound of Formula II of claim 1 in which $R_2$ and $R_3$ are hydrogen.

6. The compound of claim 1 which is 1,1'-diethyl-α,α'-thiabiscyclopentadienyl-iron-S-oxide 7. The compound of claim 1 which is 1,1'-diethyl-α,α'-thiabiscyclopentadienyl-iron-S-dioxide.

* * * * *

UNITED STATES PATENT AND TRADEMARK OFFICE
CERTIFICATE OF CORRECTION

PATENT NO. : 3,952,036
DATED : April 20, 1976
INVENTOR(S) : John T. Suh

It is certified that error appears in the above—identified patent and that said Letters Patent are hereby corrected as shown below:

In the title: "1,1-(Thiadialkylidene)" should read "1,1'-(Thiadialkylidene)". Col. 1, line 3 is blank and should read "RELATED CASES".

Signed and Sealed this

Nineteenth Day of April 1977

[SEAL]

Attest:

RUTH C. MASON
*Attesting Officer*

C. MARSHALL DANN
*Commissioner of Patents and Trademarks*